United States Patent [19]
Kolentsi

[11] Patent Number: 5,495,303
[45] Date of Patent: Feb. 27, 1996

[54] FLOATING EYEGLASSES HAVING A LATERAL FLANGE

[76] Inventor: George Kolentsi, 411 Duplex Ave., PH5, Toronto, Ontario, Canada, M4R 1V2

[21] Appl. No.: 394,119

[22] Filed: Feb. 22, 1995

[51] Int. Cl.⁶ .................................................. G02C 1/00
[52] U.S. Cl. .................................. 351/43; 351/158; 2/428
[58] Field of Search ................................. 351/43, 41, 47, 351/57, 62, 158, 124, 125, 83, 85; 2/428, 427, 426, 439, 440, 441, 451, 445

[56] References Cited

U.S. PATENT DOCUMENTS

| | | |
|---|---|---|
| 3,667,834 | 6/1972 | Davison et al. . |
| 3,740,124 | 6/1973 | Goodman et al. . |
| 4,047,809 | 9/1977 | Zuccatti . |
| 4,153,348 | 5/1979 | Walters et al. . |
| 4,670,915 | 6/1987 | Evans . |
| 4,934,807 | 6/1990 | Bolle et al. . |
| 4,955,708 | 9/1990 | Kahaney . |
| 5,319,396 | 6/1994 | Cesarczyk . |

*Primary Examiner*—William L. Sikes
*Assistant Examiner*—Hung Xuan Dang
*Attorney, Agent, or Firm*—Barrigar & Moss

[57] ABSTRACT

The invention relates to attractively designed eyeglasses which float and also protect the wearer from the impact of flying object such as hurled pebbles. The eyeglasses of the invention comprise a lens, a frame for holding the lens characterized by a top transverse frame member having an interior side including a lateral flange therealong, temple arms mounted to the frame, and a foam member adhesively bonded to the interior side of the transverse member and partially abutting the flange, the foam member having a buoyancy greater than the weight of the eyewear. The flange prevents the foam strip from being dislodged due to repeated wear and the loss of efficacy of adhesives used to bond the foam strip.

15 Claims, 3 Drawing Sheets

FLOATING EYEGLASSES HAVING A LATERAL FLANGE

FIELD OF THE INVENTION

The present invention relates to the field of eye glasses, and more particularly to floating sun-glasses.

BACKGROUND OF THE INVENTION

Sun glasses are beneficial for reducing the often times blinding effect of the sun, particularly in a marine environment wherein the surface of a body of water can cause a significant glare. In such an environment, however, persons who are involved in physical activities, such as boating, fishing, water-skiing, etc. often risk having their sunglasses fly off their faces only to disappear into the water. In addition, such persons may also be subject to receiving blows on the face by bumping into things, as for example a boater who is prone to losing his balance under turbulent water conditions. In non-marine environments, flying objects may be hurled at the wearer's face, such as pebbles dislodged by moving objects, e.g. bicycles. Such blows are not only painful, but can quite readily shatter the wearer's sunglasses.

U.S. Pat. No. 4,955,708, issued Sep. 11, 1990 to Kahaney, discloses sunglasses having a single transparent pane or lens with temple arm mounts being directly attached to said pane. A brow bar featuring a thin cushion strip secured to the inner wall surface thereof is detachably clipped to the top edge of the pane. The brow bar is meant to cushion impacts from flying particles and the like. However, these sunglasses do not float. In addition, as the pane directly supports the temple arms, the pane bears a significant load bearing stress which tends to make the eyeglasses weak with respect to absorbing the impact of hurled objects. Furthermore, the thin cushion strip is prone to being dislodged due to the repetitive motion of wearing and removing the glasses, which motion generally stresses the adhesive employed to secure the strip. This stress is particularly acute on hot summer days when the typical adhesive tends to lose its efficacy.

U.S. Pat. No. 4,934,807, issued Jun. 19, 1990 to Bolle' et. al., discloses sunglasses having a removable and replaceable transparent convex lens or pane curved both horizontally and vertically. The sunglasses include a moisture absorbing means comprising a foam absorber strip which is removably attached to the frame via female recesses formed within the frame which accept male pins depending from the strip. Due to the nature of their attachment, the foam absorber strips in these eyeglasses are not designed to withstand any significant impact shock, nor do these glasses float.

U.S. Pat. No. 3,740,124, issued Jun. 19, 1973 to Goodman and Leblanc, discloses a floatable pair of spectacles having a specific gravity of less than 1 by virtue of compartments contained within the frame which constitute a volume of not less than about 25% of the over-all volume of the frame. These glasses, while floatable, are not designed to withstand any typical shock due to their fragile construction.

U.S. Pat. No. 4,966,451, issued Oct. 30, 1990 to Corral and Lopez, discloses a temple mounted floatation device for eyeglasses which is removably attached for use during water related activities. Such a device, however, yields an unsightly appendage projecting from the eyeglasses.

There is a need in the art for protective eyewear which can absorb the impact from small particles hurled at the wearer's face and can also float in a manner so as to be easily found in a large area of water. Such glasses must necessarily be attractively designed, without any non-fashionable appendages providing buoyancy.

SUMMARY OF INVENTION

The invention provides eyeglasses which are attractively designed yet are capable of floating in water as well as protecting the wearer from the impact of hurled objects and the like. The eyeglasses of the invention feature a frame having a foam strip unobtrusively adhesively mounted to a frame of the eyeglasses for enabling the eyeglasses to float and for providing protection against impact. The frame further includes a lateral flange along an interior side thereof for preventing the foam strip from being dislodged due to the typical loss of efficacy of adhesives over time.

According to one aspect of the invention, there is provided protective eyewear comprising a lens, a frame for holding the lens characterized by a top transverse frame member having an interior side including a lateral flange therealong, temple arms mounted to the frame, and a foam member adhesively bonded to the interior side of the transverse member and partially abutting the flange, the foam member having a buoyancy greater than the total weight of the eyewear. In the preferred embodiment of the invention, the lens and the frame are curved rearwardly with respect to a horizontal plane and curved rearwardly with respect to a vertical plane so as to substantially conform to the curvature of a typical wearer's face. In addition, the preferred embodiment also includes telescopic temple arms for enabling a wearer to adjust how snug the eyeglasses fit against the wearer's face.

BRIEF DESCRIPTION OF DRAWINGS

The invention will be more fully understood with reference to the following detailed description and accompanying drawings wherein.

DETAILED DESCRIPTION OF PREFERRED EMBODIMENTS

Figure 1:
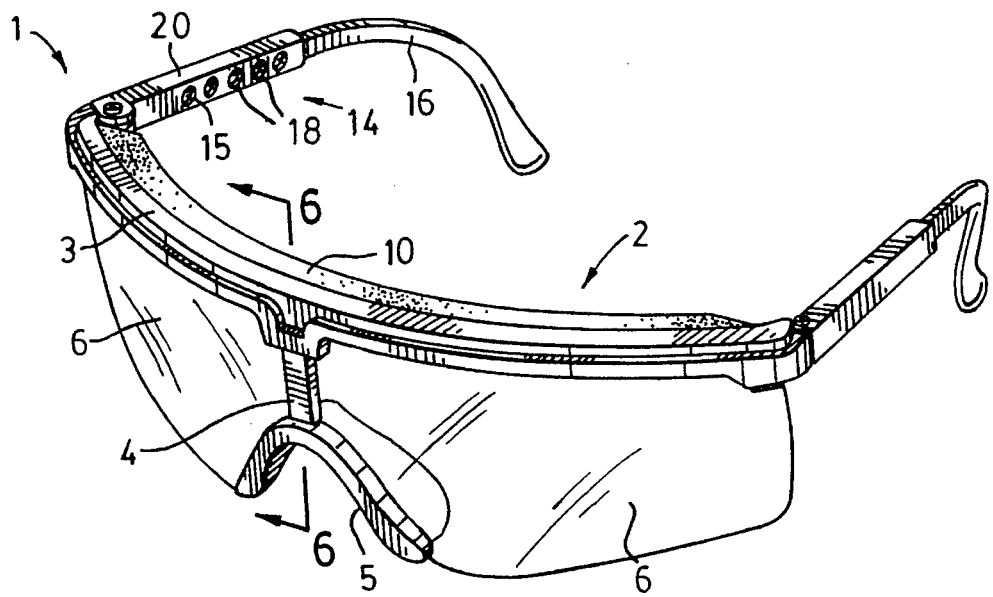
FIG. 1 is a left, front, perspective view, taken from above, of a preferred embodiment of a pair of eyeglasses in accordance with the present invention.

Referring to the drawings, a front perspective view of a preferred embodiment of a pair of protective eyeglasses is generally indicated by reference numeral 1. For the purposes of the discussion herein, the following terms are used to describe frames of reference with respect to eyeglasses 1: "interior" or "rear" refer to the side of the eyeglasses adjacent to the face; "exterior", "front" or "forward" refer to the other side. "Horizontal" and "vertical" refer respectively to the horizontal and vertical planes as seen in FIG. 1.

Figure 3:
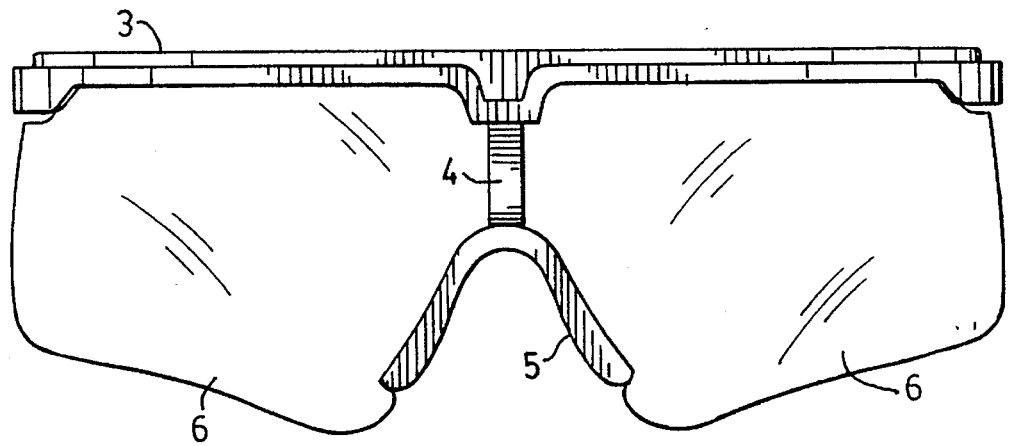
FIG. 3 is a front view of the eyeglasses of FIG. 1.
Figure 4:
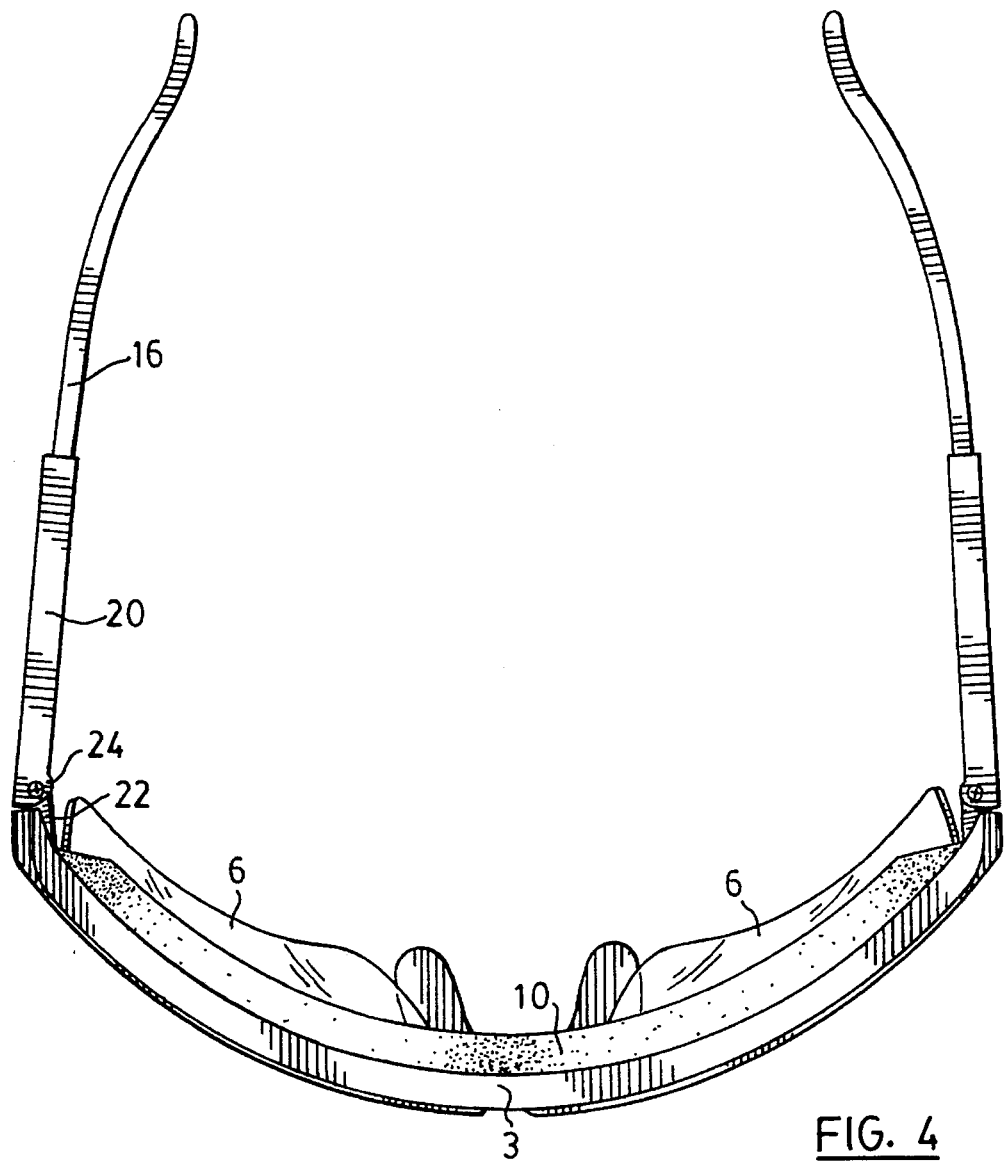
FIG. 4 is a top view of the eyeglasses of FIG. 1.

The eyeglasses 1 comprise a frame 2 composed of a transverse frame member 3, a vertical frame member 4 depending from the transverse frame member 3, and an arch-shaped nose member 5 having an apex depending from the bottom end of vertical member 4. The vertical frame member 4 is positioned so as to substantially bisect the transverse frame member 3, thereby allowing the nose member 5 to evenly balance the weight of the eyeglasses upon a wearer's nose. To assist in this function, the nose member 5 is somewhat flared, as seen best in FIG. 3, to assist in gripping the wearer's nose and spreading the weight of the eyeglasses thereon.

Figure 2:
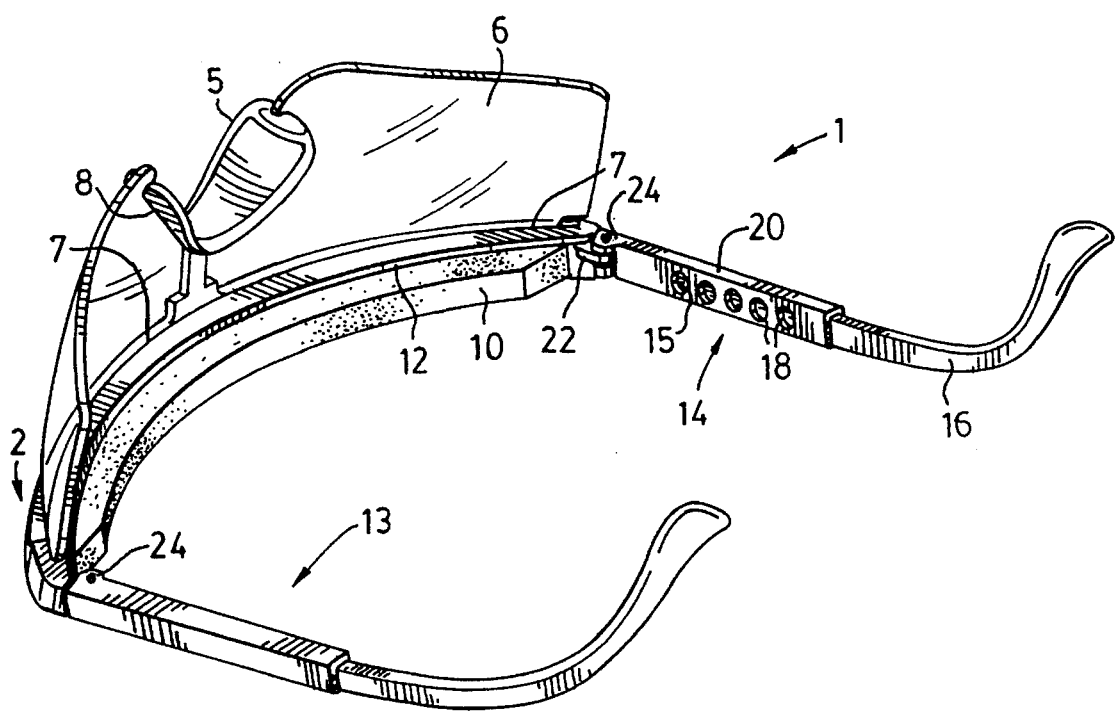
FIG. 2 is a right, rear perspective view of the eyeglasses of FIG. 1 taken from below.
Figure 6:
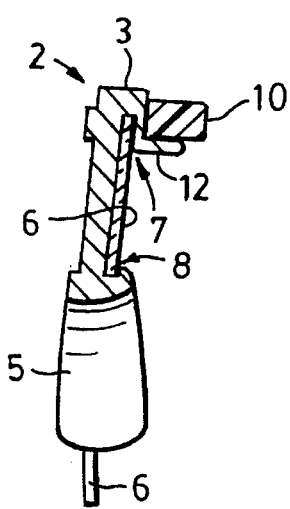
FIG. 6 is a sectional view taken along lines 6—6 of FIG. 1.

Referring in particular to FIGS. 2 and 6, the frame 2 preferably holds a single transparent or translucent convex lens or pane 6. The pane 6 is secured to the frame 2 by being located in a longitudinal pane-retaining slot 7 present in the underside of the transverse frame member 3. In addition, nose member 5 includes a pane retaining slot 8 in its top peripheral side for the same purpose. In the preferred embodiment of the present invention, vertical frame member 4 is a relatively thin member appearing only on the exterior of the eyeglasses and thus does not include any pane retaining slots and the like.

Figure 5:
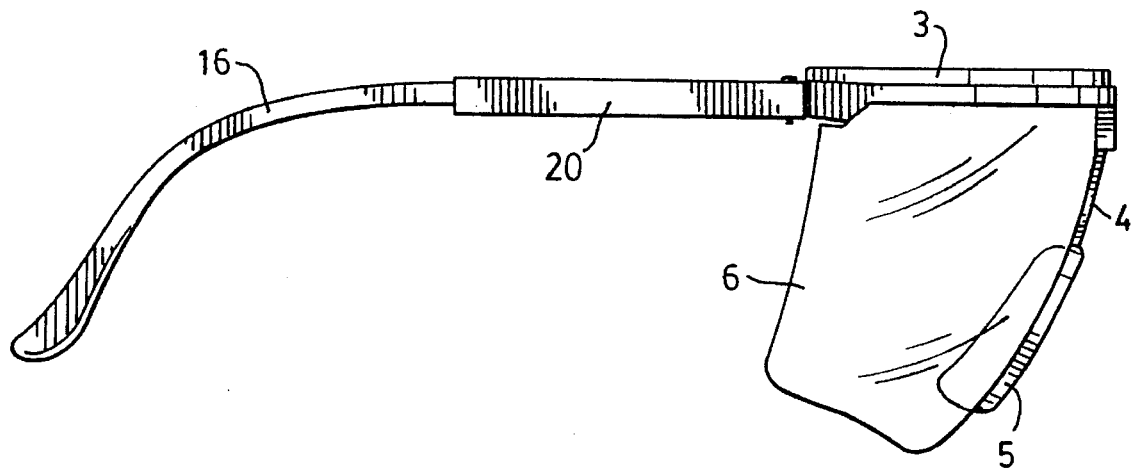
FIG. 5 is a right side view of the eyeglasses of FIG. 1, the left side (not shown) being a mirror image thereto.

The frame 2 and embedded convex pane 6, which collectively form the front face of the eyeglasses, are curved rearwardly with respect to both the horizontal and vertical planes. The width of the pane 6 and its degree of horizontal curvature are such so as to substantially wrap around or conform to the curvature of a typical wearer's face. In addition, the shape, height and vertical curvature of the pane 6 (seen best in FIG. 5) are such so as to substantially cover the space from the temple just above the eyebrows at the top to approximately following the cheek bones on the typical wearer's face at the bottom. This degree of coverage affords the typical wearer with a high level of protection from flying particles and the like which may be hurled at the wearer from a wide variety of angles. It also provides excellent coverage from the blinding effects of the sun, particularly in a marine environment or in a skiing type of environment wherein the glaring effects of the sun on the landscape may originate from a wide variety of angles.

The transverse frame member 3 includes means at opposing ends thereof for mounting temple arms 13. In the preferred embodiment of the invention, nibs 22, each having an optionally threaded hole therein, extend rearwardly from the ends of transverse member 3. Temple arms 13, each having a forked projection featuring aligned nibs 24 with registered holes therein, at least one of which is threaded, are hingeably mounted to the nibs 22 by screws as is well known in the art. Of course, nibs 22 could be placed at the ends of temple arms 13 and forked nibs 24 could be placed on transverse member 3 to provide a hinge in this manner. Other methods, as known in the art per se may also be used to hinge temple arms 13 onto frame 2, but it should be noted that temple arms 13 are not fastened directly to the pane 6 in order to avoid stressing it.

In the preferred embodiment of the invention, each temple arm 13 is telescopically adjustable, enabling the wearer to adjust how snug the eyeglasses fit against the wearer's face, and thereby providing an almost universal-fitting eyeglasses. Preferably, each temple arm 13 is comprised of a male member 16 and a female member 20, the two being secured by means of a detent-type joint 14. In this joint, the female member 20 features a series of holes 18. The male member 16 features a bump 15 which fits snugly into one of the holes 18, yet by applying a force to the male member 16 the bump 15 may be urged into any of holes 18 thereby providing the means for adjusting the length of arms 13.

Figure 7:
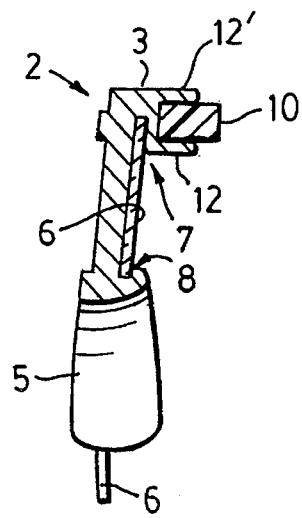
FIG. 7 is a sectional view similar to FIG. 6, but showing a flange positioned at the top of the interior side of the transverse member.

The transverse member 3 of frame 2 features a lateral flange 12 along its interior side, preferably at the bottom thereof. A foam cushion/floatation strip 10 is adhesively bonded to the interior side of the transverse member 3. The foam strip, which is somewhat wider than the flange 12 (depending upon the type of foam employed), abuts, i.e. partially rests on, the flange 12, as seen more clearly in FIG. 6. It should be appreciated that the flange 12 prevents the foam strip 10 from slipping down the frame 2 as adhesively secured foam is prone to do due to repeated wearing and removal of the eyeglasses and the natural loss of the efficacy of the adhesive, particularly on hot days. The foam strip 10 therefore remains in place. In alternative embodiments, the flange 12 may be alternatively positioned at the top of the interior side of transverse member 3, or a second flange 12 can be additionally placed thereat as illustrated in FIG. 7.

The foam strip 10 is formed from a closed-cell foam, such as ethylene vinyl acetate sponge having a density of 0.30 g/cm$^3$ and is preferably dimensioned approximately 0.25" wide, 0.25" thick and 6" long, i.e. approximately 0.5 cm high, 0.5 cm thick and 14.5 cm long. The frame material is preferably an organic plastic such as a nylon. The buoyancy provided by the exemplified foam strip is sufficient to cause the eyeglasses to float at or near the surface of the water provided that the frame 2, pane 6 and temple arms are constructed from suitable lightweight materials such that the eyeglasses have a specific gravity of less than 1. The foamstrip 10 can alternatively be constructed in other suitable dimensions from various types of foams embodying variously sized intercellular spaces so long as the foam's buoyancy, i.e. the upward force experienced by the foam strip when disposed in a body of water due to the pressure differential therein, is greater than the weight of the eyeglasses (including all components). The foam strip 10 must also be large enough, e.g. at least 5 mm thick, to comfortably cushion the wearer's forehead from the impact of hurled pebbles and the like, as well as isolate the frame 2, including the flange 12, from contacting the wearer's face. It should be noted that these dual functions of cushioning and floatation are produced in an inconspicuous manner thereby enabling the eyeglasses to remain fashionable, e.g. without any unsightly floatation appendages or the like.

A further advantage provided by the foam strip 10 and its positioning on the frame 2 lies in the manner by which the eyeglasses float. In a large body of water such as a lake, it is difficult to find a relatively small, dark-coloured object as sunglasses are prone to be. With the present invention however, the eyeglasses float such that the arms of the glasses remain submerged in water whereas the front face of the glasses tend to rise to the surface of the water. Hence, as the translucent pane floats on or very near to the surface of the water, it tends to reflect the light from the sun, moon or artificial light source thereby making the glasses easier to spot due to the glinting thereof.

Although a preferred embodiment of the invention has been described in detail herein with reference to the accompanying drawings, it is to be understood that the invention is not limited to the precise embodiment, and that various changes and modifications may be effected therein without departing from the scope or spirit of the invention.

I claim:

1. Floating eyeglasses comprising:

a lens;

a frame for holding said lens characterized by a top transverse frame member having an interior side including a lateral flange therealong;

temple arms mounted to said frame; and a foam member adhesively bonded to the interior side of said transverse member and partially abutting the flange, the foam member having a buoyancy greater than the weight of the eyeglasses.

2. Floating eyeglasses according to claim 1 wherein said foam member is a closed-cell type of foam.

3. Floating eyeglasses according to claim 2 wherein said foam member is dimensioned approximately 0.5 cm wide, 0.5 cm thick and 15.0 cm long.

4. Floating eyeglasses according to claim 3 wherein said foam member is constructed from ethylene vinyl acetate sponge having a density of about 0.30 g/cm$^3$.

5. Floating eyeglasses according to claim 3 wherein said frame and temple arms are constructed from nylon.

6. Floating eyeglasses according to claim 1 wherein said temple arms are telescopic.

7. Floating eyeglasses according to claim 6 wherein said telescopic temple arms comprise a male member featuring a bump thereon and an elongate female member featuring a plurality of holes formed in a wall thereof, the bump and a given hole adapted to provide a detent-type joint for securing the male member to the female member.

8. Floating eyeglasses according to claim 1 wherein said flange is positioned at the bottom of said interior side of said transverse member.

9. Floating eyeglasses according to claim 1 wherein said flange is positioned at the top of said interior side of said transverse member.

10. Floating eyeglasses according to claim 9 including a second flange positioned at the bottom of said interior side of said transverse member.

11. Floating eyeglasses according to claim 1 wherein said lens and said frame are curved rearwardly with respect to a horizontal plane and curved rearwardly with respect to a vertical plane so as to substantially conform to the curvature of a typical wearer's face.

12. Floating eyeglasses combination comprising at least one lens, a frame having a top transverse frame member for holding the at least one lens and temple arms hingeably mounted to said frame, an improvement characterized by the top transverse frame member featuring a lateral flange along the interior side thereof and a foam member adhesively mounted to the interior side of the transverse member and partially abutting the flange, the foam member having a buoyancy greater than the total weight of the eyeglasses.

13. Floating eyeglasses combination according to claim 12 wherein said flange is positioned at the bottom of the interior side of said transverse member.

14. Floating eyeglasses combination according to claim 12 wherein said flange is positioned at the top of the interior side of said transverse member.

15. Floating eyeglasses combination according to claim 14 including a second flange positioned at the bottom of the interior side of said transverse member.

* * * * *